United States Patent [19]

Hunt

[11] Patent Number: 4,743,593
[45] Date of Patent: May 10, 1988

[54] 9,11-O-METHYLENE DERIVATIVES OF 9-DIHYDROERYTHROMYCIN

[75] Inventor: Eric Hunt, Betchworth, England

[73] Assignee: Beecham Group p.l.c., England

[21] Appl. No.: 806,026

[22] Filed: Dec. 6, 1985

[30] Foreign Application Priority Data

Dec. 8, 1984 [GB] United Kingdom ............ 8431055
Sep. 24, 1985 [GB] United Kingdom ............ 8523580
Oct. 5, 1985 [GB] United Kingdom ............ 8524620

[51] Int. Cl.$^4$ .................... A61K 31/70; C07H 17/8
[52] U.S. Cl. ................................. 514/29; 536/7.2
[58] Field of Search ........................ 536/7.2; 514/29

[56] References Cited

U.S. PATENT DOCUMENTS

| | | | |
|---|---|---|---|
| 3,524,844 | 8/1970 | Keller-Juslen et al. | 536/18.1 |
| 3,884,903 | 5/1975 | Jones et al. | 536/7.2 |
| 3,884,904 | 5/1975 | Jones et al. | 536/7.2 |
| 4,382,085 | 5/1983 | Sciavolino et al. | 536/7.2 |
| 4,382,086 | 5/1983 | Sciavolino . | |

FOREIGN PATENT DOCUMENTS

2515075 10/1976 Fed. Rep of Germany .

OTHER PUBLICATIONS

Chem. Abs. 91: 91936c (1979), European Search Report, EP 85 30 8754.

Primary Examiner—J. R. Brown
Assistant Examiner—Elli Peselev
Attorney, Agent, or Firm—Jacobs & Jacobs

[57] ABSTRACT

An antibacterially active 9,11-O-methylene derivative of 9-dihydroerythromycin wherein the methylene group is optionally substituted by one or two hydrocarbon groups. In particular, compounds of formula I and their pharmaceutically acceptable esters and acid addition salts:

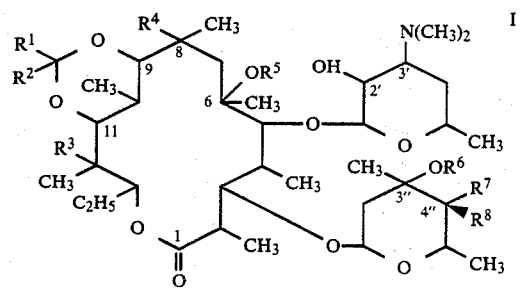

wherein:
  $R^1$ and $R^2$ are each H, optionally substituted hydrocarbon, or optionally substituted 5 or 6-membered O or S heterocyclyl, or
  $R^1 + R^2$ is optionally substituted divalent hydrocarbon,
  $R^3$ is H or OH;
  $R^4$ is H, F or OH;
  $R^5$ and $R^6$ are each H of $CH_3$;
  one of $R^7$ and $R^8$ is H, OH, alkoxy, alkanoyloxy optionally substituted $NH_2$, or $R^9$—$SO_2$—O—, and the other of $R^7$ and $R^8$ is H, or
  $R^7 + R^8$ is oxo, oxime or substituted oxime; and $R^9$ is organic.

25 Claims, No Drawings

9,11-O-METHYLENE DERIVATIVES OF 9-DIHYDROERYTHROMYCIN

The present invention relates to novel chemical compounds, their preparation and their use, and in particular to a novel class of erythromycin derivatives. These compounds have antibacterial properties, in particular against Gram-positive bacteria but also against some Gram-negative bacteria, and they are therefore of use in the treatment of bacterial infections in humans and animals caused by a wide range of organisms.

Erythromycin was first described in U.S. Pat. No. 2,653,899 (R. L. Bunch et al; Eli Lilly). The structure of erythromycins can be represented as follows:

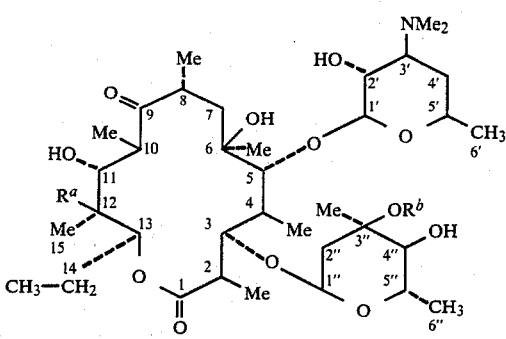

in which
$R^a$ denotes hydrogen or hydroxy and
$R^b$ denotes hydrogen or methyl.

The basic erythromycin structure comprises:
(i) a 14-membered lactone ring, referred to as the erythronolide ring, numbered with unprimed digits as shown in the above formula,
(ii) a first sugar ring, known as the desosamine ring, numbered with single-primed digits, and
(iii) a second sugar ring, known as the cladinose ring, numbered with double-primed digits.

The erythronolide ring can exist in two forms:
erythronolide A (in which $R^a$=OH)
erythronolide B (in which $R^a$=H).

The four main naturally occurring erythromycins are as follows:

| Erythromycin | $R^a$ | $R^b$ |
|---|---|---|
| A | OH | CH₃ |
| B | H | CH₃ |
| C | OH | H |
| D | H | H | of which erythromycin A is by far the most important.

Erythromycins, and in particular erythromycin A, are antibiotics widely employed clinically in the treatment of infections caused by Gram-positive and some Gram-negative bacteria. A major drawback of erythromycins is their poor acid stability, resulting in poor and erratic oral absorption.

Numerous attempts have been made to modify erythromycin to produce derivatives having improved acid stability without loss of the antibacterial activity.

(9S)-9-Dihydroerythromycin A (which carries a 9-hydroxy group in place of the 9-keto group) has been described, but has poor antibacterial activity (P. F. Wiley et al, *J. Amer. Chem. Soc.*, 1955, 77, 3676–3677; M. V. Sigal et al, ibid, 1956, 78, 388–395; and T. Glabski et al, *Roczniki Chem.*, 1976, 50, 1281). Erythromycylamine and erythromycin oxime (in which the 9-keto group is replaced, respectively, by an amino or oxime group), as well as various N-substituted derivatives of erythromycylamine have also been described (GB No. 1 100 504 (Pliva Pharmaceutical); E. H. Massey et al, *Tetrahedron Letters*, 1970, No. 2, 157–160; and G. H. Timms et al, ibid, 1971, No. 2, 195–198), as have various erythromycin oxime ethers (U.S. Pat. No. 3,681,326 (A.M. Von Esch; Abbott Laboratories); U.S. Pat. No. 3,869,445 and U.S. Pat. No. 4,063,014 (both R. Hallas et al; Abbott Laboratories); U.S. Pat. No. 4,349,545 (S. Gouin d'Ambrieres; Roussel-Uclaf)); and *Antimicrobial agents and chemotherapy*, 1974, 6 479).

Certain aldehyde-erythromycylamine condensation products with a 9-N,6-O- or 9-N,11-O-cyclic substituent have previously been disclosed (U.S. Pat. No. 4,048,306 (R. Maier et al; Boehringer Ingelheim GmbH)).

4″-Deoxy-11-O-methylthiomethyl-4″-oxo-erythromycin B and its conversion to (i) 4″-deoxy-9,11-O-(optionally substituted)methylene-4″-oxo-erythromycin B 6,9-hemiacetal and the corresponding 4″-epi-hydroxy, 2′,4″-O-diacetyl-4″-epi, and 4″-O-acetyl-4″-epi derivatives, and (ii) 4″-deoxy-4″-oxo-, 4″-O-acetyl-4″-epi-, and 4″-epi-erythromycin B; as well as 4″-O-formyl-11-O-methylthiomethyl-erythromycin B and its conversion to 11-O-methylthiomethyl-erythromycin B, 9,11-O-methylene-erythromycin B 6,9-hemiacetal, 11-O-methyl-erythromycin B and 11-O-n-butylerythromycin B; and also 4″-deoxy-4″-oxo-erythromycin A are described in U.S. Pat. No. 3,842,069, U.S. Pat. No. 3,884,903 and U.S. Pat. No. 3,884,904 (all P. H. Jones et al; Abbott Laboratories).

4″-Deoxy-4″-amino-erythromycin A, 4″-deoxy-4″-amino-erythromycin A 6,9-hemiketal, and 4″-deoxy-4″-oxo-erythromycin A 6,9-hemiketal, as well as corresponding 11-O-acetyl and 11,12-cyclic carbonate derivatives, and also 4″-deoxy-4″-amino-erythromycin B and 4″-deoxy-4″-oxo-erythromycin A 4″-O-oxime or 4″-O-acetyloxime, are described in U.S. Pat. No. 4,150,220 (F. C. Sciavolino; Pfizer).

An 11,12l -cyclic carbonate of 9-dihydroerythromycin has also been described in T. Glabski et al; *Roczniki Chem.*, 1976, 50, 1281 and 9-dihydro-11,12-O-isopropylidene-erythromycin A and the corresponding 4″-epi compound have been described in U.S. Pat. No. 4,382,086 (F. C. Sciavolino et al; Pfizer).

6-O-Methyl-, 6,11-di-O-methyl-, 11-O-methyl- and 11-O-ethyl-erythromycin A, and also 6-O-methyl-6,4″-di-O-methyl-, and 6,11,4″-tri-O-methyl-erythromycin B are described in EP No. 0 041 355 A1, EP O No. 080 818 A1 and EP O No. 080 819 A1 (all Taisho Pharmaceutical).

The erythromycin derivatives according to the present invention possess improved acid stability as compared with erythromycin A while retaining good antibacterial activity.

The present invention provides antibacterially active 9,11-O-methylene derivatives of 9-dihydroerythromycin wherein the methylene group is optionally substituted.

In particular, the present invention provides a compound of the general formula I or a pharmaceutically acceptable ester or acid addition salt thereof:

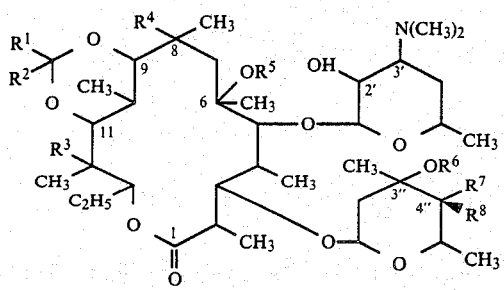

wherein
each of $R^1$ and $R^2$, which may be identical or different, denotes hydrogen, an unsubstituted or substituted hydrocarbon group, or an unsubstituted or substituted 5- or 6-membered heterocyclyl group containing an oxygen or sulphur atom as the heteroatom, or $R^1$ and $R^2$ together denote an unsubstituted or substituted divalent hydrocarbon group (especially an alkylene group), or an unsubstituted or substituted alkyleneoxyalkylene or alkylenethioalkylene group;

$R^3$ denotes hydrogen or hydroxy;

$R^4$ denotes hydrogen, fluorine or hydroxy;

each of $R^5$ and $R^6$, which may be identical or different, denotes hydrogen or methyl;

one of $R^7$ and $R^8$ denotes hydrogen, hydroxy, alkoxy, alkanoyloxy, amino, substituted amino, or a group of the formula $R^9$—$SO_2$—O—, and the other of $R^7$ and $R^8$ denotes hydrogen, or $R^7$ and $R^8$ together denote an oxo group, an oxime group, or a substituted oxime group; and $R^9$ denotes an organic group.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, aryl, $(C_{3-7})$cycloalkyl$(C_{1-6})$alkyl, aryl$(C_{1-6})$alkyl, $(C_{1-6})$alkyl$(C_{3-7})$cycloalkyl, and $(C_{1-6})$alkylaryl.

Examples of suitable optional substituents for the above-mentioned hydrocarbon groups include, heterocylyl, amino, $(C_{1-6})$alkanoylamino, (mono, di, or tri)-$(C_{1-6})$alkylamino, hydroxy, $(C_{1-6})$alkoxy, $(C_{1-6})$alkoxy$(C_{1-6})$alkoxy, aryloxy, mercapto, $(C_{1-6})$alkylthio, heterocyclylthio, arylthio, sulphamoyl, carbamoyl, substituted carbamoyl, amidino, guanidino, nitro, chloro, bromo, fluoro, carboxy and salts and esters thereof, $(C_{1-6})$alkanoyloxy, arylcarbonyloxy, heterocyclylcarbonyloxy, acyl, and acyloxy groups.

Any alkyl group or moiety referred to herein may be straight or branched, unsubstituted or substituted, and may contain, for example, up to 12 carbon atoms, suitably up to 6 carbon atoms. In particular, the alkyl group or moiety may be an unsubstituted or substituted methyl, ethyl, n-propyl, iso-propyl, n-butyl, sec-butyl, isobutyl or tert-butyl group. Examples of suitable optional substitutents for any such alkyl group or moiety include the above-listed substitutents for hydrocarbon groups, and also the above-listed non-alkyl hydrocarbon groups, for example $(C_{2-6})$alkenyl and aryl groups.

The term 'aryl' as used herein includes phenyl and naphthyl, which may be unsubstituted or substituted by up to five, preferably up to three, groups selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkylcarbonyloxy, and $(C_{1-6})$alkylcarbonyl groups, and also the other above-listed substituents for hydrocarbon groups, and the other above-listed non-aryl hydrocarbon groups.

The compounds according to the present invention, of the general formula I, are 9,11-acetal and 9,11-ketal derivatives of 9-dihydroerythromycin. The present compounds can exist in two isomeric forms at the 9-position, namely the (9S)-isomer and the (9R)-isomer. The (9S)-isomer is preferred.

A hydrocarbon group denoted by $R^1$ or $R^2$ may suitably be an unsubstituted or substituted alkyl or aryl group. Advantageously, the alkyl group may be a lower alkyl group, for example a $(C_{1-6})$alkyl group. Advantageously, the aryl group may be a phenyl group.

A heterocyclyl group denoted by $R^1$ or $R^2$ may suitably be a furyl, thienyl, dihydrofuryl, tetrahydrofuryl, dihydrothienyl, tetrahydrothienyl, pyranyl, dihydropyranyl, tetrahydropyranyl, thiapyranyl, dihydrothiapyranyl or tetrahydrothiapyranyl ring.

Suitably, at least one of $R^1$ and $R^2$ denotes hydrogen.

$R^1$ and $R^2$ together may suitably denote an alkylene group, optionally interrupted, in a non-terminal position, by an oxygen or sulphur atom, such that $R^1$ and $R^2$ together with the carbon atom to which they are attached denote a carbocyclic group (for example, a cyclohexyl group) or a heterocyclic group bonded through a carbon atom that is not adjacent to a heteroatom (for example, a tetrahydrofuryl, tetrahydrothienyl, tetrahydropyranyl or tetrahydrothiapyranyl group).

In preferred compounds of the general formula I, one of $R^1$ and $R^2$ denotes hydrogen and the other of $R^1$ and $R^2$ denotes hydrogen or unsubstituted or substituted alkyl (especially lower alkyl) or unsubstituted or substituted aryl (especially phenyl) or unsubstituted or substituted heterocyclyl (especially furyl).

Examples of suitable substituents for a hydrocarbon or heterocyclyl group $R^1$ and/or $R^2$ and for a divalent group $R^1 + R^2$ include, in particular, alkoxy, alkoxyalkoxy, aryloxy, hydroxy, amino, substituted amino (for example, monoalkylamino and dialkylamino), carboxy, esterified carboxy (for example, alkoxycarbonyl), acyloxy (wherein 'acyl' means organic-carbonyl) (for example, alkanoyloxy), carbamoyl ($H_2N$—C(=O)—), and substituted carbamoyl (for example, N-alkylcarbamoyl and N,N-dialkylcarbamoyl) groups. Any alkyl moiety in such substituents may itself be substituted by, for example, one of the listed substituents, and any alkyl moiety advantageously contains not more than 6, preferably not more than 4, carbon atoms. An example of a substituent in which an alkyl moiety is itself substituted is the alkoxyalkoxy substituent.

In the compounds of the general formula I, preferably $R^3$ denotes a hydroxy group as in the erythronolide A ring, or, in other words, the compounds of the general formula I are preferably derivatives of erythromycin A. Alternatively, however, the present compounds may be derivatives of erythromycin B, in which case $R^3$ denotes a hydrogen atom, or of another naturally occurring erythromycin.

The 8-position of the erythronolide ring preferably has only a methyl substitutent, as in naturally-occuring erythromycins, and therefore preferably $R^4$ denotes a hydrogen atom. 8-Hydroxy and 8-fluoro derivatives have been described (J. Antibiotics, XXVI 575–581

(1973) and XXXVI, 1439-1450 (1983) and $R^4$ may denote a hydroxy group or a fluorine atom.

The —$OR^5$ group in the 6-position in the general formula I is preferably a hydroxy group as in naturally-occuring erythromycins, but it may alternatively be a methoxy group. 6-O-methyl derivatives of erythromycin are described in EP O No. 0 041 355 Al (Y. Watanabe et al; Taisho Pharmaceutical Co. Ltd.).

The —$OR^6$ group in the 3"-position of the cladinose ring may be a hydroxy group or a methoxy group. Preferably, $R^6$ denotes a methyl group as in erythromycin A and B.

The 4"-position of the cladinose ring may suitably carry a hydroxy group as in erythromycin A and B ($R^7$=H, $R^8$=OH). Various modifications of the 4"-position of the cladinose ring have previously been described and those modifications may be incorporated in the compounds according to the present invention:

(i) 4"-deoxy-4"-oxo derivatives ($R^7+R^8$=O=) are described in U.S. Pat. No. 3,842,069, U.S. Pat. No. 3,884,903 and U.S. Pat. No. 4,150,220, all op. cit.;

(ii) 4"-epi-hydroxy derivatives ($R^7$=OH; $R^8$=H) and 4"-deoxy-4"-alkanoyloxy-4"-epi derivatives ($R^7$=alkanoyloxy, especially $CH_3COO$—; $R^8$=H) are described in U.S. Pat. No. 3,884,903, op. cit.;

(iii) 4"-O-alkyl derivatives ($R^7$ or $R^8$=alkoxy, especially methoxy; the other of $R^7$ and $R^8$=H) are described in EP O No. 080 818 Al, op. cit.;

(iv) 4"-deoxy-4"-amino derivatives ($R^7$ or $R^8$=amino or substituted amino; the other of $R^7$ and $R^8$=H) are described in U.S. Pat. No. 4,150,220, op. cit.;

(v) 4"-deoxy-4"-oxime derivatives ($R^7+R^8$=oxime (=N—OH) or substituted oxime, especially acetyloxime (=N—O—CO—$CH_3$)) are also described in U.S. Pat. No. 4,150,220, op cit.;

(vi) 4"-O-sulphonyl derivatives ($R^7$=H, $R^8$=$R^9$—$SO_2$—O—) are described in U.S. Pat. No. 3,836,519, U.S. Pat. No. 3,869,445 and U.S. Pat. No. 4,063,014 (all R. Hallas et al; Abbott Laboratories); and (vii) 4"-deoxy derivatives ($R^7$=$R^8$=H) are described in JP No. 58-049396 (Toyo Jozo KK).

In the 4"-deoxy-4"-(substituted amino) derivatives, the substituted amino group $R^7$ or $R^8$ may suitably be a group of the formula —$NHCOR^C$ or —$NHSO_2R^C$ in which $R^C$ denotes a hydrocarbon group.

In the 4"-O-sulphonyl derivatives, in which $R^7$ or $R^8$ denotes a sulphonyloxy group of the formula $R^9$—$SO_2$—O—, the organic group $R^9$ may suitably be an unsubstituted or substituted hydrocarbon or oxahydrocarbon group, thiahydrocarbon or azahydrocarbon group, more especially an alkyl, alkenyl, unsubstituted or substituted aryl (especially phenyl, nitrophenyl, halophenyl or alkylphenyl), unsubstituted or substituted aralkyl (especially benzyl, nitrobenzyl, halobenzyl or alkylbenzyl), unsubstituted or substituted aryloxyalkyl (especially phenoxyalkyl, nitrophenoxyalkyl, halophenoxyalkyl or alkylphenoxyalkyl), or substituted ethyl (especially $R^D$—$CH_2$—$CH_2$—, wherein $R^D$ is defined as below) group.

Examples of groups $R^D$ in the 4"-substituent $R^D$—$CH_2$—$CH_2$—$SO_2$—O— include amino, substituted amino, carbamoyl, substituted carbamoyl, sulphamoyl, substituted sulphamoyl, substituted ureido, substituted thioureido, alkoxy, alkythio, optionally substituted aryloxy, optionally substituted arylthio, optionally substituted benzyloxy, optionally substituted benzylthio, substituted suphonyl, substituted sulphinyl, substituted alkyl, substituted alkanoyl, substituted cyano, and other groups more specifically described in U.S. Pat. No. 3,869,445 and U.S. Pat. No. 4,063,014, op. cit.

Preferably, $R^9$ denotes a hydrocarbon group, particularly a ($C_{1-6}$)alkyl group, especially a methyl group.

The present invention includes pharmaceutically acceptable esters, especially in vivo hydrolysable esters, of the compounds of the general formula I. Such esters may be formed at any hydroxy group in the compounds of the general formula I, but usually the ester will be formed at the 2'-hydroxy group of the desosamine ring, thus giving a 2'-O-acyl derivative of the type described in U.S. Pat. No. 2,862,921 (R. E. Booth et al; Upjohn Co.), U.S. Pat. No. 2,993,833 (V. C. Stephens; Eli Lilly), U.S. Pat. No. 3,836,519, U.S. Pat. No. 3,842,069, U.S. Pat. No. 3,869,445, U.S. Pat. No. 3,884,903, U.S. Pat. No. 3,884,904 and U.S. Pat. No. 4,150,220, all op. cit.

Suitable pharmaceutically acceptable in vivo hydrolysable esters include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include acetates, propionates, butyrates, acrylates, and ethylsuccinates.

The present invention also includes acid addition salts, especially pharmaceutically acceptable acid addition salts, of the compounds of the general formula I. Such acid addition salts may, in particular, be formed at the 3'-dimethylamino group of the desosamine ring.

Various acid addition salts of erythromycin are described in U.S. Pat. No. 2,761,859 (C. E. Hoffhine, Jr.; Abbott Laboratories) and U.S. Pat. No. 2,852,429 (J. T. Shepler; Eli Lilly).

Suitable acid addition salts of the compounds of the invention include pharmaceutically acceptable inorganic acid addition salts, for example the sulphate, nitrate, phosphate, borate, hydrochloride and hydrobromide, and also pharmaceutically acceptable organic acid addition salts, for example the acetate, tartrate, maleate, citrate, succinate, benzoate, ascorbate, methane-sulphate, α-keto-glutarate, α-glycerophosphate, and glucose-1-phosphate. Preferably the acid addition salt is the laurylsulphate salt.

Examples of individual compounds according to the present invention include:

(i) 9,11-O-ethylidene-9-dihydroerythromycin A (in general formula I, $R^1$=$CH_3$, $R^2$=H, $R^3$=OH, $R^4$=$R^5$=H, $R^6$=$CH_3$, $R^7$=H, $R^8$=OH);

(ii) 9,11-O-methylene-9-dihydroerythromycin A (in general formula I, $R^1$=$R^2$=H, $R^3$ to $R^8$ as for compound (i));

(iii) 9,11-O-isopropylidene-9-dihydroerythromycin A (in general formula I, $R^1$=$R^2$=$CH_3$, $R^3$ to $R^8$ as for compound (i));

(iv) 9,11-O-propylidene-9-dihydroerythromycin A (in general formula I, $R^1=C_2H_5$, $R^2=H$, $R^3$ to $R^8$ as for compound (i));

(v) 9,11-O-benzylidene-9-dihydroerythromycin A (in general formula I, $R^1=$ phenyl, $R^2=H$, $R^3$ to $R^8$ as for compound (i));

(vi) 9,11-O-n-butylidene-9-dihydroerythromycin A (in general formula I, $R^1=C_3H_7$, $R^2=H$, $R^3$ to $R^8$ as for compound (i));

(vii) 9,11-O-isobutylidene-9-dihydroerythromycin A (in general formula I, $R^1=(CH_3)_2CH-$, $R_2=H$, $R^3$ to $R^8$ as for compound (i)); and (viii) 9,11-O-furfurylidene-9-dihydroerythromycin A (in general formula I, $R^1=$ furyl, $R^2=H$, $R^3$ to $R^8$ as for compound (i));

as well as the corresponding 6-O-methyl derivatives, the corresponding derivatives in which the 8-position and/or the 4''-position is modified as discussed above; and also pharmaceutically acceptable esters and acid addition salts of such compounds.

The 9,11-O-methylene erythromycin derivatives according to the invention may be prepared by reacting an erythromycin derivative having hydroxy substituents at the 9- and 11-positions, in which any reactive groups (other than the 9- and 11-hydroxy groups) may optionally be protected, with an aldehyde or ketone or reactive derivative thereof; and thereafter if necessary carrying out one or more of the following steps:

(a) converting a substitutent on the erythromycin structure to another such substituent in a conventional manner;

(b) removing any protecting groups; and (c) forming a pharmaceutically acceptable ester or acid addition salt.

More particularly, a compound of the general formula I as hereinbefore defined or a pharmaceutically acceptable ester or acid addition salt thereof may be prepared by a process which comprises reacting a compound of the general formula II:

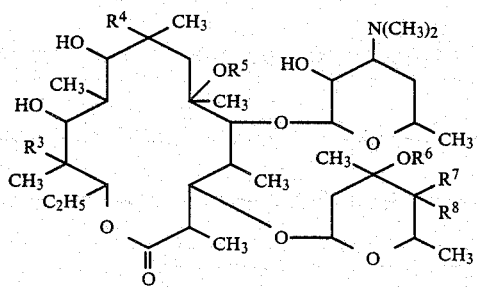

wherein $R^3$, $R^4$, $R^5$, $R^6$, $R^7$ and $R^8$ are defined as above with respect to general formula I, in which compound of the general formula II any reactive group (other than the 9-hydroxy and 11-hydroxy groups) may optionally be protected, with:

(i) a compound of the general formula III:

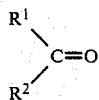

in which $R^1$ and $R^2$ are defined as above with respect to general formula I, or a reactive derivative of such a compound; or (ii) a compound of the general formula IV

in which $R^1$ and $R^2$ are defined as above with respect to general formula I; and each of X and Y, which may be identical or different, denotes a readily displaceable group;

and thereafter removing any protecting group that may be present;

and optionally (a) converting any one or more of groups $R^5$, $R^7$ and $R^8$ to another such group; and/or (b) forming a pharmaceutically acceptable ester or acid addition salt.

The compound of the general formula II in which:

each of $R^3$ and $R^8$ denotes hydroxy, each of $R^4$, $R^5$ and $R^7$ denotes hydrogen, and $R^6$ denotes methyl is 9-dihydroerythromycin A, which may be prepared by known methods, for example by reduction of erythromycin A with sodium borohydride or sodium trimethoxyborohydride. The reduction may, for example be effected as described in the above-cited references relating to 9-dihydroerythromycin A.

The compound of the general formula II in which:

each of $R^3$, $R^4$, $R^5$ and $R^7$ denotes hydrogen, and $R^6$ denotes methyl, and $R^8$ denotes hydroxy is 9-dihydroerythromycin B, and may be prepared by reduction of erythromycin B, for example by analogous known methods.

Other compounds of the general formula II may also be prepared, by methods known per se, from erythromycin A or B or the corresponding 9-dihydro derivative. For example, a compound in which the 6-position, the 8-position or the 4''-position is substituted other than as in naturally-occuring erythromycin A or B (that is to say, in which $R^5$ is methyl, or in which $R^4$ is hydroxy or fluoro, or in which $R^7$ is other than hydrogen and/or $R^8$ is other than hydroxy) may be prepared as described in the respective references cited above.

In general, in the preparation of compounds of the general formula II, the reduction of the 9-oxo group of erythromycin A or B to a 9-hydroxy group may be effected prior to or subsequent to modification of other positions of the erythromycin molecule.

Prior to carrying out the reaction of a compound of the general formula II with a compound of the general formula III or a reactive derivative thereof or with a compound of the general formula IV, any reactive group of a compound of the general formula II may optionally be protected.

In particular, the 3'-dimethylamino group may be protected by an N-protecting group. The N-protection may be effected in known manner, for example by the method described by E. H. Flynn et al, (J. Amer. Chem. Soc., 1955, 77, 3104–3106).

Examples of suitable N-protecting groups include benzyloxycarbonyl, and substituted benzyloxycarbonyl, (for example, p-methylbenzyloxycarbonyl, p-nitrobenzyloxycarbonyl, p-bromobenzyloxycarbonyl, p-phenylazobenzyloxycarbonyl, and p-(p'-methoxyphenylazo)-benzyloxycarbonyl). A preferred N-protecting group is benzyloxycarbonyl.

It may also be advantageous to protect one or more of the hydroxy groups present in the erythromycin molecule (other than the 9- and 11-hydroxy groups) prior to reaction. In particular, it may be advantageous to protect any hydroxy groups present at the 2'- and 4"-positions, especially the 2'-hydroxy group. It is convenient to employ the same group to protect the hydroxy group(s) as that employed to protect the amino moiety, especially a benzyloxycarbonyl group.

Any reactive substituents that may be present in the group $R^7$ or $R^8$ should preferably also be protected in a conventional manner.

The present invention also provides compounds of the general formula V, which are useful as intermediates in the preparation of the compounds of the general formula I:

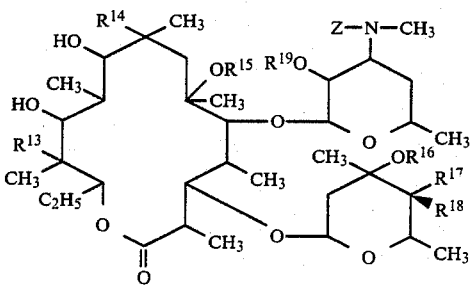

in which
$R^{13}$ denotes H or OH;
$R^{14}$ denotes H, F or OH;
$R^{15}$ denotes H or $CH_3$;
$R^{16}$ denotes H or $CH_3$;
one of $R^{17}$ and $R^{18}$ denotes H, OH, OZ, $NZ_2$, $NH_2$, NHZ, substituted $NH_2$, substituted NHZ, alkanoyloxy, or $R^9$—$SO_2$—O— (in which $R^9$ denotes an organic group), and the other of $R^{17}$ and $R^{18}$ denotes H, or
$R^{17}$ and $R^{18}$ together denote oxo;
$R^{19}$ denotes H or Z; and
Z denotes a protecting group, more particularly an N-protecting group, preferably a substituted benzyloxycarbonyl group or, especially, a benzyloxycarbonyl group.

In method (i) of the process according to the invention, the compound of the general formula II, optionally containing protective groups, is reacted with an aldehyde ($R^1$ and/or $R^2$=H) or a ketone ($R^1$, $R^2$ are not H) of the general formula III or a reactive derivative thereof. Suitable reactive derivatives of aldehydes or ketones of the general formula III include, for example, acetals of the general formula VI

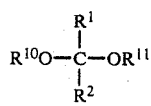

hemiacetals of the general formula VII

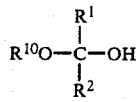

and
enol ethers of the general formula VIII

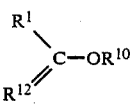

in which formula VI to VIII,
$R^1$ and $R^2$ are defined as above with respect to general formula I;
each of $R^{10}$ and $R^{11}$, which may be identical or different, denotes a hydrocarbon group, advantageously a $(C_{1-6})$hydrocarbon group, preferably an alkyl group, especially a methyl or ethyl group; and
$R^{12}$ denotes an optionally substituted divalent hydrocarbon group corresponding to an optionally substituted monovalent hydrocarbon group $R^2$ with the loss of a hydrogen atom on the carbon atom carrying the free valency.

The reaction according to method (i) is suitably carried out in the presence of an acid catalyst. Preferred acid catalysts include pyridinium salts, for example pyridinium tosylate and pyridinium chloride. Other suitable acid catalysts include, for example, zinc chloride, cupric sulphate, boron trifluoride etherate, and organic sulphonic acids (for example, p-toluenesulphonic acid), optionally in conjunction with, for example, tertiary organic bases (for example, pyridine, dimethylpyridines, and trimethylpyridines).

Advantageously, the reaction is also carried out in the presence of a drying agent, for example anhydrous calcium sulphate, magnesium sulphate, sodium sulphate, cupric sulphate, or molecular sieves.

The reaction according to method (i) may suitably be carried out in an inert solvent. Suitable solvents include, for example, ether solvents (for example, tetrahydrofuran, dioxan, ethoxyethane, and 1,2-dimethoxyethane), halogenated solvents (for example, chloroform and methylated chloride), and aromatic solvents (for example, toluene).

The reaction according to method (i) may suitably be effected at a cool to slightly elevated temperature, preferably at ambient temperature. The reaction may, for example, be effected at a temperature within the range of from $-30°$ C. to $+30°$ C., preferably from $0°$ C. to $+30°$ C., especially from $+10°$ C. to $+25°$ C.

In method (ii) of the process according to the invention, the compound of the general formula II, optionally containing protective groups, is reacted with a compound of the general formula IV. In general formula IV, each of X and Y, which may be identical to one another but are preferably different from one another, denotes a leaving group.

Examples of suitable leaving groups X and Y include halogen atoms (for example chlorine, bromine, and iodine), alkylsulphonyloxy groups (for example methanesulphonyloxy), and arylsulphonyloxy groups (for example p-toluenesulphonyloxy).

Preferably, each of X and Y denotes a halogen atom, especially different halogen atoms. More preferably X denotes chlorine or bromine and Y denotes bromine or iodine. A compound of the general formula IV in which X denotes chlorine and Y denotes iodine is especially preferred.

The reaction according to method (ii) is suitably carried out under strongly basic conditions. Examples of suitable strong bases include sodium hydride, potassium hydride, lithium amide, sodium amide, potassium amide, potassium t-butoxide, butyllithium, and lithium diisopropylamide.

The reaction according to method (ii) may suitably be carried out in an inert solvent. Suitable solvents include, for example, polar aprotic solvents (for example, N,N-dimethylformamide, N,N-dimethylacetamide, dimethylsulphoxide, hexamethylphosphoric triamide, and N-methylpyrrolidinone and mixtures of two or more such solvents) and mixtures of one or more polar aprotic solvents with one or more ether solvents (for example, tetrahydrofuran, dioxan, ethoxyethane, and 1,2-dimethoxyethane.

The reaction according to method (ii) may suitably be effected at a cool to ambient temperature preferably at a cool temperature. The reaction may, for example, be effected at a temperature within the range of from $-30°$ C. to $+30°$ C., preferably from $-5°$ C. to $+20°$ C., especially from $0°$ C. to $+15°$ C.

After completion of the reaction according to method (i) or (ii) above, and preferably prior to removal of any protecting groups, any of the groups $R^5$, $R^7$ and $R^8$ may be converted to any of the other such groups within the definitions given above by methods known in the art, for example by the methods disclosed in the publications mentioned above. For example, a compound in which $R^8$ denotes hydrogen and $R^7$ denotes hydroxy can be converted to a compound in which $R^7$ and $R^8$ together denote oxo and optionally thereafter to a compound in which $R^8$ denotes hydroxy or acetoxy and $R^7$ denotes hydrogen by methods analogous to those described in U.S. Pat. No. 3,884,903, op.cit.

After completion of the reaction according to method (i) or (ii) above and after the optional conversion of any groups $R^5$, $R^7$ and $R^8$, any protecting groups may be removed by a conventional method. It is preferable to employ a hydrogenation procedure.

The hydrogenation may suitably be carried out in the presence of a transition metal catalyst, for example palladium, which may, for example, be in the form of palladium on carbon (charcoal), palladium on barium sulphate, palladium on calcium carbonate, or palladium black. A favoured catalyst is palladium on carbon (sometimes referred to as palladium on charcoal); for example 5%, 10%, 20% or 30% palladium on carbon. A low, medium or high pressure of hydrogen may be used in this reaction, for example a pressure of from 1 to 6 atmospheres absolute, a pressure of 1 atmosphere absolute being convenient. The reaction may suitably be carried out at a non-extreme temperature, for example at a temperature within the range of from $0°$ C. to $30°$ C., preferably from $12°$ C. to $25°$ C. It is generally convenient to carry out the reaction at ambient temperature. The reaction is preferably carried out at a pH within the range of from 4.5 to 5.0, which may be maintained by the use of a suitable buffer, for example an acetate buffer at pH 4.8. Suitable solvents for carrying out the hydrogenation include ethanol, n-propanol, isopropanol, tetrahydrofuran, dioxan, ethyl acetate, a mixture of two or more such solvents, or such a solvent or mixture in the presence of water. A favoured solvent is ethanol.

In order to restore the dimethylamino group at the 3'-position, it is convenient to effect a reductive methylation, which advantageously may be carried out at the same time as the reductive removal of the protecting groups, as in the method of Flynn et al, op.cit.

A compound of the general formula I may be converted to a pharmaceutically acceptable salt thereof or ester thereof in a conventional manner at any convenient stage in the manufacturing process, for example before or after the removal of any protecting groups and/or before or after any conversion of groups $R^5$, $R^7$ and $R^8$ to other such groups.

Isolation and purification of a compound according to the invention may be carried out using conventional methods, and may include a chromatography step. Preferably the product is isolated in crystalline form.

The compounds according to the invention, that is to say, the compounds of the general formula I and their pharmaceutically acceptable salts and esters, have antibacterial properties and are useful for the treatment of bacterial infections in animals, especially mammals, including humans, in particular humans and domesticated animals (including farm animals). The compounds may be used for the treatment of infections caused by a wide range of gram-positive and gram-negative organisms including, for example, *Bacillus subtilis, Corynebacterium xerosis, Sarcina lutea, Staphylococcus aureus, Streptococcus faecalis, Streptococcus pyogenes, Streptococcus agalactiae, Streptococcus pneumoniae, Haemophilus sp. Neisseria sp., Chlamydia sp.,* and *Legionella sp.*

The compounds according to the invention are suitably provided in substantially pure form, for example at least 50% pure, advantageously at least 75% pure, preferably at least 95% pure, especially at least 98% pure, all percentages being calculated as weight/weight. An impure or less pure form of a compound according to the invention may, for example, be used in the preparation of a more pure form of the same compound or of a related compound (for example, a corresponding salt, ester or free acid) suitable for pharmaceutical use. Although the purity of any compound used as an intermediate may be less critical than that of a compound used as a final product, for example one used directly for pharmaceutical use (for example in a composition according to the invention as described below), nevertheless such an intermediate compound is advantageously provided in substantially pure form. It is generally advantageous to provide the compounds according to the invention in crystalline form, optionally hydrated or solvated crystalline form.

The present invention provides a pharmaceutical composition comprising a compound according to the invention together with a pharmaceutically acceptable carrier or excipient.

The present invention also provides a method of treating bacterial infections in animals, especially in humans and in domesticated mammals, which comprises administering a compound or composition according to the invention to a patient in need thereof.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colouring agents.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.5 to 50 mg/kg of body weight. For an adult human (of approximately 70 kg body weight), from 100 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferably from 50 to 500 mg, of a compound according to the invention.

No adverse toxicological effects are indicated when the compounds according to the invention are administered within the above-mentioned dosage ranges.

The following examples illustrate the preparation of compounds according to the present invention.

EXAMPLE 1

(9S)-9,11-O-Ethylidene-9-dihydroerythromycin A (a) (9S)-9,11-O-Ethylidene-9-dihydro-2'-O,N-dibenzyloxycarbonyl-des-N-methylerythromycin A (9S)-9-Dihydro-2'-O,N-dibenzyloxycarbonyl-des-N-methyl erythromycin A (700 mg), pyridinium tosylate (70 mg), and acetaldehyde (3.5 ml) were dissolved in dry tetrahydrofuran (6.5 ml). Anhydrous calcium sulphate (1.0 g) was added and the mixture was stirred for 67 h. The mixture was diluted with ethyl acetate (50 ml) and filtered. The filtrate was washed with water ($2 \times 30$ ml) and dried ($Na_2SO_4$). The solvent was removed and the resulting residue was chromatographed on silica gel using ethyl acetate-hexane as eluent. The title compound was thus obtained as a colourless gum (500 mg); $[\alpha]_D^{20} = -65.0°$ (3.1% wt/vol. in $CHCl_3$).

(b) (9S)-9,11-O-Ethylidene-9-dihydroerythromycin A

The compound from 1(a) (350 mg) was dissolved in a mixture of ethanol (15 ml) and acetate buffer (pH 4.8; 1.2 ml) and the solution was shaken with 10% palladium-charcoal (100 mg) under hydrogen (1 atmosphere) for 30 min. 37% Formaldehyde solution (1.5 ml) was added and the hydrogenation was continued for 1.5 h. The catalyst was removed by filtration and was washed with ethanol and water. The ethanol was removed from the filtrate under reduced pressure and the residue was diluted to about 30 ml with water. The solution was basified (approx. pH 11) using potassium carbonate and was extracted with ethyl acetate ($2 \times 30$ ml). The combined extracts were washed with water (20 ml) and dried ($Na_2SO_4$). The solvent was removed to give the title compound as a colourless foam (270 mg); $[\alpha]_D^{20} = -31.2°$ (1.0% wt/vol in $CHCl_3$); $\nu_{max}$ ($CHCl_3$) 3570, 3440 and 1725 $cm^{-1}$; mass spectrum, $M^+$, 761.4931 ($C_{39}H_{71}NO_{13}$ requires M, 761.4929).

EXAMPLE 2

(9S)-9,11-O-Methylene-9-dihydroerythromycin A (a) (9S)-9,11-O-Methylene-9-dihydro-2'-O,N-dibenzyloxycarbonyl-des-N-methylerythromycin A (9S)-9-Dihydro-2'-O,N-dibenzyloxycarbonyl-des-N-methylerythromycin A (800 mg) in dry N,N-dimethylformamide (10 ml) was treated with anhydrous potassium carbonate powder (500 mg), 15-Crown-5 ether (1,4,7,10,13-pentaoxacyclopentadecane) (2 drops), and chloroiodomethane (1 ml). The mixture was stirred and ice-cooled while sodium hydride (50% dispersion in oil; 100 mg) was added in one portion. The mixture was stirred and ice-cooled for 30 min, and then the cooling bath was removed and stirring was continued for 10 min. The mixture was diluted with ethyl acetate (100 ml) and washed with diluted $Na_2SO_3$ (30 ml) and water ($3 \times 40$ ml). The solution was dried ($Na_2SO_4$) and the solvent was removed under reduced pressure. The residue was chromatographed on silica gel using ethyl acetate-hexane as eluent. The title compound was thus obtained as colourless crystals (520 mg), m.p. 118°–119° C. (ether-hexane); $[\alpha]_D^{21} = -74.3°$ (1.35% wt/vol in $CHCl_3$). (Found: C, 63.6%; H, 7.9%, N, 1.35%. $C_{53}H_{79}NO_{17}$ requires C, 63.5%; H, 7.95%; N, 1.4%).

(b) (9S)-9,11-O-Methylene-9-dihydroerythromycin A

The compound from (2a) was converted into the title compound using a procedure analogous to that described in Example 1(b). The title compound was obtained as colourless crystals, m.p. 140°–142° C. (methylene chloride-hexane); $[\alpha]_D^{25} = -63.3°$ (1.0% wt/vol in CHCl$_3$); mass spectrum, M$^+$, 747.4761 (C$_{38}$H$_{69}$NO$_{13}$ requires M, 747.4752).

EXAMPLE 3

(9S)-9,11-O-Isopropylidene-9-dihydroerythromycin A (9S)-9-Dihydroerythromycin A (500 mg) and 2-methoxypropene (0.7 ml) were dissolved in dry ethanol-free chloroform (10 ml). Pyridinium chloride (120 mg) was added and the mixture was stirred for 16 h. The solution was washed with potassium carbonate solution and then dried (Na$_2$SO$_4$). The solvent was removed and the residue was dissolved in a mixture of acetone (10 ml) and water (10 ml). The solution was brought to pH 3.5 using 1M HCl, and allowed to stand for 2 h. The solution was basified using potassium carbonate and extracted with ethyl acetate. The solution was dried (Na$_2$SO$_4$) and the solvent was removed to yield a colourless gum (420 mg). The gum was chromatographed on silanised silica gel using 3:2 methanol-phosphate buffer (0.067M, pH 7) as eluent. The title compound was obtained as a colourless foam (320 mg); $[\alpha]_D^{25} = -30.4°$ (1.0% wt/vol in CHCl$_3$); $\nu_{max}$ (CHCl$_3$) 3530, 3400 and 1725 cm$^{-1}$; mass spectrum, M$^+$, 775.5106 (C$_{40}$H$_{73}$NO$_{13}$ requires M, 775.5082).

EXAMPLE 4

(9S)-9,11-O-Propylidene-9-dihydroerythromycin A (a) (9S)9,11-O-Propylidene-9-dihydro-2'-O,N-dibenzyloxycarbonyl-des-N-methylerythromycin A (9S)-9-Dihydro-2'-O,N-dibenzyloxycarbonyl-des-N-methylerythromycin A (500 mg) and pyridinium tosylate (70 mg) were dissolved in a mixture of 1,2-dimethoxyethane (5 ml) and propionaldehyde (5 ml). Anhydrous calcium sulphate (1.0 g) was added and the mixture was stirred for 10 days. The mixture was diluted with ethyl acetate (50 ml) and filtered. The filtrate was washed with water (2×30 ml) and dried (Na$_2$SO$_4$). The solvent was removed and the resulting gum was chromatographed to give the title compound as a colourless gum (105 mg); $[\alpha]_D^{22} = -62.5°$ (1.0% wt/vol in CHCl$_3$).

(b) (9S)-9,11-O-Propylidiene-9-dihydroerythromycin A

The product from 4(a) was converted into the title compound using a procedure analogous to that described in Example 1(b). The title compound was obtained as colourless crystals, m.p. 127°–129° C. (methylene chloride-hexane); $[\alpha]_D° = -36.0°$ (1.0% wt/vol in CHCl$_3$); $\nu_{max}$ (CHCl$_3$) 3530, 3440 and 1725 cm$^{-1}$.

EXAMPLE 5

(9S)-9,11-O-n-Butylidene-9-dihydroerythromycin A

Using a method analogous to that described in Example 4, but with n-butyraldehyde in place of propionaldehyde, the title compound was prepared as colourless crystals, $[\alpha]_D° = -38.6°$ (1.0% wt/vol in CHCl$_3$).

EXAMPLE 6

(9S)-9,11-O-iso-Butylidene-9-dihydroerythromycin A

Using a method analogous to that described in Example 4, but with iso-butyraldehyde in place of propionaldehyde, the title compound was prepared as colourless crystals, $[\alpha]_D° = -35.5°$ (1.0% wt/vol in CHCl$_3$).

EXAMPLE 7

(9S)-9,11-O-Benzylidene-9-dihydroerythromcyin A (9S)-9-Dihydroerythromycin A (370 mg) in benzaldehyde (1 ml) was treated with pyridinium p-toluenesulphonate (125 mg) and anhydrous copper(II) sulphate (300 mg). The mixture was stirred at room temperature for 7 days. The mixture was diluted with ethyl acetate (50 ml) and stirred with powdered potassium carbonate (1.0 g). The mixture was filtered and the filtrate was washed twice the water. The solution was dried (Na$_2$SO$_4$) and the solvent was evaporated under reduced pressure to yield a blue-coloured oil. The oil was chromatgraphed on silanised silica gel using 3:2 methanol-phosphate buffer (0.067M, pH 7.0) to give the title compound as colourless crystals (50 mg); R$_f$ 0.16; $\nu_{max}$ (CHCl$_3$) 3520, 3450 and 1725 cm$^{-1}$.

EXAMPLE 8

(9S)-9,11-O-Furfurylidene-9-dihydroerythromycin A (9S)-9-Dihydroerythromycin A (370 mg) and pyridinium p-toluenesulphonate (130 mg) in freshly distilled furfuraldehyde (1.2 ml) was treated with anhydrous copper(II) sulphate (300 mg) and the mixture was stirred at room temperature in the dark for 10 days. The mixture was diluted with ethyl acetate (50 ml) and washed with potassium carbonate solution (30 ml) and water (3×20 ml). The solution was dried (Na$_2$SO$_4$) and the solvent was evaporated under reduced pressure to yield a brown oil. The oil was chromatographed on silanised silica gel using 1:1 to 3:2. methanol-phosphate buffer (0.067M, pH 7.0) to give the title compound as a pale yellow foam (45 mg), $[\alpha]_D^{20} = -45.8°$ (1.0% wt/vol in CHCl$_3$); M$^+$, 813.4898 (C$_{42}$H$_{71}$NO$_{14}$ requires M, 813.4878).

EXAMPLE 9

(9S)-9,11-O-Ethylidene-9-dihydroerythromycin A (9S)-9-Dihydroerythromycin A (1.0 g) and pyridinium p-toluenesulphonate (360 mg) in acetaldehyde (5 ml) was treated with anhydrous copper(II) sulphate (1.0 g) and the mixture was stirred at room temperature for 10 days. The mixture was diluted with ethyl acetate (50 ml) and washed with potassium carbonate solution (30 ml) and water (3×30 ml). The solution was dried (Na$_2$SO$_4$) and the solvent was removed under reduced pressure to give a blue coloured foam. The foam was chromatographed on silanised silica gel using 1:1 to 3:2 methanol-phosphate buffer (0.067M, pH 7.0) to give the title compound as colourless crystals (500 mg), m.p. 143°–145° C. (dichloromethane-hexane) (Found: C, 61.2; H, 9.4; N, 1.75. C$_{39}$H$_{71}$NO$_{13}$ required C, 61.45; H, 9.4; N, 1.85%); other properties as for the sample from Example 1(b).

EXAMPLE 10

(9S)-9,11-O-Isopropylidene-9-dihydroerythromycin A (9S)-9-Dihydroerythromycin A (500 mg) in dry ethanol-free chloroform (10 ml) was treated with 2,2-dimethoxypropane (2 ml) and pyridinium chloride (120 mg). The mixture was stired at room temperature for 14 days. The mixture was diluted with chloroform (50 ml) and washed with potassium carbonate solution (30 ml) and water (30 ml). The solution was dried (Na$_2$SO$_4$) and the solvent was removed under reduced pressure to give a colourless foam. The foam was chromatographed on silanised silica gel using 1:1 to 3:2 methanol-phosphate buffer (0.067M, pH 7.0) to give the title compound as a colourless foam (90 mg). The product had the same properties as those described for the sample from Example 3.

I claim:
1. A compound of the formula (I):

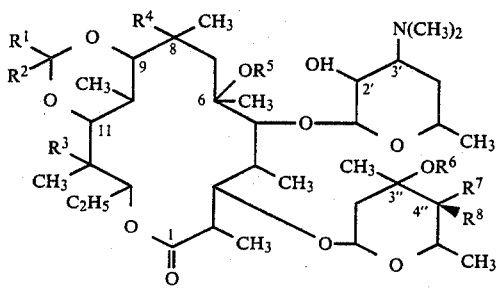

a pharmaceutically acceptable acid addition salt thereof or a pharmaceutically acceptable ester thereof wherein:
$R^1$ and $R^2$ are the same or different and each is hydrogen, an unsubstituted or substituted hydrocarbon moiety of up to 18 carbon atoms, an unsubstituted or substituted 5- or 6-membered heterocyclyl having one heteroatom selected from the group consisting of oxygen and sulphur, or $R^1$ and $R^2$ together form an unsubstituted or substituted divalent hydrocarbon group of up to 18 carbon atoms, or an unsubstituted or substituted alkyleneoxyalkylene or alkylenethioalkylene moiety containing up to 12 carbon atoms in each alkyl moiety;
$R^3$ is hydrogen or hydroxy;
$R^4$ is hydrogen, fluoro or hydroxy;
$R^5$ and $R^6$ are the same or different and each is hydrogen or methyl;
one of $R^7$ and $R^8$ is hydrogen, hydroxy, alkoxy of up to 12 carbon atoms, alkanoyloxy of up to 12 carbon atoms, amino, substituted amino or a moiety of the formula $R^9$—$SO_2$—O— and the other of $R^7$ and $R^8$ is hydrogen, or $R^7$ and $R^8$ togetheer form an oxo moiety, an oxime moiety or a substituted oxime moiety; and
$R^9$ is an unsubstituted or substituted hydrocarbon, oxahydrocarbon, thiahydrocarbon or azahydrocarbon of up to 18 carbon atoms;
when any of the above specified moieties are substituted, the substituents are selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

2. A compound according to claim 1, a pharmaceutically acceptable acid addition salt or pharmaceutically acceptable ester thereof wherein the hydrocarbon moieties have up to 10 carbon atoms.

3. A compound according to claim 1, a pharmaceutically acceptable acid addition salt or pharmaceutically acceptable ester thereof wherein the hydrocarbon moieties have up to 6 carbon atoms.

4. A compound according to claim 1, a pharmaceutically acceptable acid addition salt thereof or a pharmaceutically acceptable ester thereof wherein $R^1$ and $R^2$ are the same or different and each is hydrogen, alkyl of up to 6 carbon atoms, aryl or a 5- 6-membered heterocyclyl having one heteroatom selected from the group consisting of oxygen and sulphur said moieties other than hydrogen being unsubstituted or substituted; when the alkyl moiety is substituted the substituent is one or more members selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxy; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkyl of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanolyamino of 1 to 6 carbon atoms in the alkyl moiety, mono-, di- or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclylcarbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

5. A compound according to claim 1, a pharmaceutically acceptable acid addition salt thereof or a pharmaceutically acceptable ester thereof wherein at least one of $R^1$ and $R^2$ is hydrogen.

6. A compound according to claim 1, a pharmaceutically acceptable acid addition salt thereof or a pharmaceutically acceptable ester thereof wherein one of $R^1$ and $R^2$ is hydrogen and the other is unsubstituted or substituted alkyl of up to 6 carbon atoms or aryl, when the alkyl moiety is substituted the substituent is one or more members selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxy; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkyl of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanolyamino of 1 to 6 carbon atoms in the alkyl moiety, mono-, di- or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclyl-carbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyl, acyl and acyloxy.

7. A compound according to claim 1, a pharmaceutically acceptable acid addition salt thereof or a pharmaceutically acceptable ester thereof wherein $R^3$ is hydroxy; $R^4$ is hydrogen; and $R^6$ is methyl.

8. A compound according to claim 1 selected from the group consisting of
9,11-O-ethylidene-9-dihydroerythromycin A;
9,11-O-methylene-9-dihydroerythromycin A;
9,11-O-isopropylidene-9-dihydroerythromycin A;
9,11-O-propylidene-9-dihydroerythromycin A;
9,11-O-benzylidene-9-dihydroerythromycin A;
9,11-O-n-butylidene-9-dihydroerythromycin A;
9,11-O-isobutylidene-9-dihydroerythromycin A; and
9,11-O-furfurylidene-9-dihydroerythromycin A.

9. A pharmaceutical composition useful for treating bacterial infections in humans and animals which comprises an antibacterially effective amount of a compound of the formula (I):

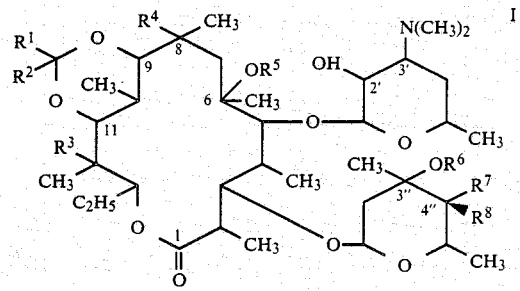

a pharmaceutically acceptable acid addition salt thereof or a pharmaceutically acceptable ester thereof wherein:
$R^1$ and $R^2$ are the same or different and each is hydrogen, an unsubstituted or substituted hydrocarbon moiety of up to 18 carbon atoms, an unsubstituted or substituted 5- or 6-membered heterocyclyl having one heteroatom selected from the group consisting of oxygen and sulphur, or $R^1$ and $R^2$ together form an unsubstituted or substituted divalent hydrocarbon group of up to 18 carbon atoms, or an unsubstituted or substituted alkyleneoxyalkylene or alkylenethioalkylene moiety containing up to 12 carbon atoms in each alkyl moiety; to 12 carbon atoms in each alkyl moiety;
$R^3$ is hydrogen or hydroxy;
$R^4$ is hydrogen, fluoro or hydroxy;
$R^5$ and $R^6$ are the same or different and each is hydrogen or methyl;
one of $R^7$ and $R^8$ is hydrogen, hydroxy, alkoxy of up to 12 carbon atoms, alkanoyloxy of up to 12 carbon atoms, amino, substituted amino or a moiety of the formula $R^9-SO_2-O-$ and the other of $R^7$ and $R^8$ is hydrogen, or $R^7$ and $R^8$ together form an oxo moiety, an oxime moiety or a substituted oxime moiety; and
$R^9$ is an unsubstituted or substituted hydrocarbon, oxahydrocarbon, thiahydrocarbon or azahydrocarbon of up to 18 carbon atoms;
when any of the above specified moieties are substituted, the substituents are selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy, in combination with a pharmaceutically acceptable carrier.

10. A composition according to claim 9 wherein the hydrocarbon moieties have up to 10 carbon atoms.

11. A composition according to claim 9 wherein the hydrocarbon moieties have up to 6 carbon atoms.

12. A composition according to claim 9 wherein $R^1$ and $R^2$ are the same or different and each is hydrogen, alkyl of up to 6 carbon atoms, aryl or a 5- or 6-membered heterocyclyl having one heteroatom selected from the group consisting of oxygen and sulphur said moieties other than hydrogen being unsubstituted or substituted; when the alkyl moiety is substituted the substituent is one or more members selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxy; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkyl of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanolyamino of 1 to 6 carbon atoms in the alkyl moiety, mono-, di or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclylcarbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

13. A composition according to claim 9 wherein at least one of $R^1$ and $R^2$ is hydrogen;
one of $R^1$ and $R^2$ is hydrogen and the other is alkyl of up to 6 carbon atoms or aryl unsubstituted or substituted by a substituent selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy, substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

14. A composition according to claim 9 wherein one of $R^1$ and $R^2$ is hydrogen and the other is unsubstituted or substituted alkyl of up to 6 carbon atoms or aryl, when the alkyl moiety is substituted the substituent is one or more members selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxyl; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkoxy of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanolyamino of 1 to 6 carbon atoms in the alkyl moiety, mono-, di or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclylcarbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

15. A composition according to claim 9 wherein $R^3$ is hydroxy; $R^4$ is hydrogen; and $R^6$ is methyl.

16. A composition according to claim 9 wherein the compound is selected from the group consisting of
9,11-O-ethylidene-9-dihydroerythromycin A;
9,11-O-methylene-9-dihydroerythromycin A;
9,11-O-isopropylidene-9-dihydroerythromycin A;
9,11-O-propylidene-9-dihydroerythromycin A;
9,11-O-benzylidene-9-dihydroerythromycin A;
9,11-O-n-butylidene-9-dihydroerythromycin A;
9,11-O-isobutylidene-9-dihydroerythromycin A; and
9,11-O-furfurylidene-9-dihydroerythromycin A.

17. A method of treating bacterial infections in humans and animals which comprises administering to a human or animal in need thereof an antibacterially effective amount of a compound of the formula (I):

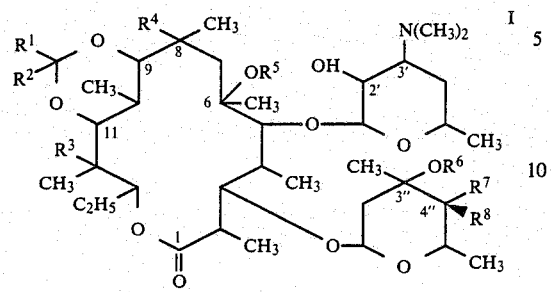

a pharmaceutically acceptable acid addition salt thereof or a pharmaceutically acceptable ester thereof wherein:
$R^1$ and $R^2$ are the same or different and each is hydrogen, an unsubstituted or substituted hydrocarbon moiety of up to 18 carbon atoms, an unsubstituted or substituted 5- or 6-membered heterocyclyl having one heteroatom selected from the group consisting of oxygen and sulphur, or $R^1$ and $R^2$ together form an unsubstituted or substituted divalent hydrocarbon group of up to 18 carbon atoms, or an unsubstituted or substituted alkyleneoxyalkylene or alkylenethioalkylene moiety containing up to 12 carbon atoms in each alkyl moiety;
$R^3$ is hydrogen or hydroxy;
$R^4$ is hydrogen, fluoro or hydroxy;
$R^5$ and $R^6$ are the same or different and each is hydrogen or methyl;
one of $R^7$ and $R^8$ is hydrogen, hydroxy, alkoxy of up to 12 carbon atoms, alkanoyloxy of up to 12 carbon atoms, amino, substituted amino or a moiety of the formula $R^9—SO_2—O—$ and the other of $R^7$ and $R^8$ is hydrogen, or $R^7$ and $R^8$ together form an oxo moiety, an oxime moiety or a substituted oxime moiety; and
$R^9$ is an unsubstituted or substituted hydrocarbon, oxahydrocarbon, thiahydrocarbon or azahydrocarbon of up to 18 carbon atoms;
when any of the above specified moieties are substituted, the substituents are selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy, in combination with a pharmaceutically acceptable carrier.

18. A method according to claim 17 wherein the hydrocarbon moieties have up to 10 carbon atoms.

19. A method according to claim 17 wherein the hydrocarbon moieties have up to 6 carbon atoms.

20. A method according to claim 17 wherein $R^1$ and $R^2$ are the same or different and each is hydrogen, alkyl of up to 6 carbon atoms, aryl, or a 5- or 6-membered heterocyclyl having one heteroatom selected from the group consisting of oxygen and sulphur, said moieties other than hydrogen being unsubstituted or substituted; when the alkyl moiety is substituted the substituent is one or more members selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxy; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkyl of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanolyamino of 1 to 6 carbon atoms in the alkyl moiety, mono-, di- or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclylcarbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di or trialkylamino of 1 to 6 carbon atoms in each alkyl moiety, hydroxy, alkoxy of 1 to 6 carbon atoms, alkoxy-substituted alkoxy of 1 to 6 carbon atoms in ech alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

21. A method according to claim 17 wherein at least one of $R^1$ and $R^2$ is hydrogen.

22. A method according to claim 17 wherein one of $R^1$ and $R^2$ is hydrogen and the other is unsubstituted or substituted alkyl of up to 6 carbon atoms or aryl, when the alkyl moiety is substituted the substituent is one or more members selected from the group consisting of heterocyclyl, amino, alkanoylamino of 1 to 6 carbon atoms in the alkyl moiety, mono-, di-, or trialkylamino of 1 to 6 carbon atoms in each alkyl moiety, hydroxy, alkenyl of 2 to 6 carbon atoms, cycloalkyl of 3 to 7 carbon atoms, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, aryl, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl, and acyloxy; when the aryl moiety is substituted, the substituents are up to five moieties selected from the group consisting of halo, alkyl of 1 to 6 carbon atoms, phenyl, aryloxy, arylthio, alkoxy of 1 to 6 carbon atoms, haloalkyl of 1 to 6 carbon atoms, hydroxy, amino, nitro, carboxy, alkoxycarbonyl of 1 to 6 carbon atoms in the alkoxy moiety, alkoxycarbonylalkyl of 1 to 6 carbon atoms in each of the alkoxy and alkyl moieties, alkylcarbonyloxy of 1 to 6 carbon atoms in the alkyl moiety and alkylcarbonyl of 1 to 6 carbon atoms in the alkyl moiety, or one or more moieties selected from the group consisting of heterocyclyl, amino, alkanoylamino of 1 to 6 carbon atoms in the alkyl moiety, mono-, di- or trialkylamino of 1 to 6 carbon atoms in each alkyl moiety, alkoxy-substituted alkoxy of 1 to 6 carbon atoms in each alkoxy moiety, mercapto, alkylthio of 1 to 6 carbon atoms in the alkyl moiety, heterocyclylthio, sulphamoyl, carbamoyl, substituted carbamoyl, amidino, guanidino, chloro, bromo, fluoro, carboxy or a salt or ester thereof, alkanoyloxy of 1 to 6 carbon atoms in the alkyl moiety, heterocyclylcarbonyloxy, acyl and acyloxy; and when the heterocyclyl moiety is substituted, the substituent is selected from the group consisting of heterocyclyl, amino, alkanoylamino of 1 to 6 carbon atoms in the alkyl moiety, mono-, di- or trialkylamino of 1 to 6 carbon atoms in each alkyl moiety, hydroxy, alkoxy of 1 to 6 carbon atoms, alkoxy-substituted alkoxy of 1 to 6 carbon atoms in each alkoxy moiety, aryloxy, mercapto, alkylthio of 1 to 6 carbon atoms in the alkyl moiety, heterocyclylthio, arylthio, sulphamoyl, carbamoyl, substituted carbamoyl, amidino, guanidino, nitro, chloro, bromo, fluoro, carboxy or a salt or ester thereof, alkanoyloxy of 1 to 6 carbon atoms in the alkyl moiety, arylcarbonyloxy, heterocyclylcarbonyloxy, acyl and acyloxy.

23. A method according to claim 17 wherein $R^3$ is hydroxy; $R^4$ is hydrogen; and $R^6$ is methyl.

24. A method according to claim 17 wherein the compound is selected from the group consisting of 9,11-O-ethylidene-9-dihydroerythromycin A;
9,11-O-methylene-9-dihydroerythromycin A;
9,11-O-isopropylidene-9-dihydroerythromycin A;
9,11-O-propylidine-9-dihydroerythromycin A;
9,11-O-benzylidene-9-dihydroerythromycin A;
9,11-O-n-butylidene-9-dihydroerythromycin A;
9,11-O-isobutylidene-9-dihydroerythromycin A; and
9,11-O-furfurylidene-9-dihydroerythromycin A.

25. A compound of the formula (V):

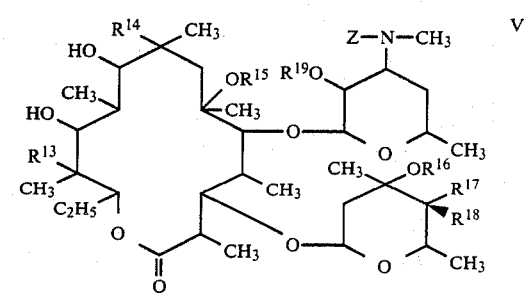

wherein
$R^{13}$ is hydrogen or hydroxyl;
$R^{14}$ is hydrogen, fluoro or hydroxyl;
$R^{15}$ is hydrogen or methyl;
$R^{16}$ is hydrogen or methyl;
one of $R^{17}$ and $R^{18}$ is hydrogen, hydroxyl, OZ, $NZ_2$, $NH_2$, NHZ, substituted amino, substituted NHZ, alkanoyloxy of up to 12 carbon atoms or $R^9$—$SO_2$—O— wherein $R^9$ is an unsubstituted or substituted hydrocarbon, oxahydrocarbon, thiahydrocarbon or azahydrocarbon of up to 18 carbon atoms and the other of $R^{17}$ and $R^{18}$ is hydrogen or $R^{17}$ and $R^{18}$ together form an oxo moiety;
$R^{19}$ is hydrogen or Z; and
Z is benzyloxycarbonyl unsubstituted or substituted by a substituent selected from the group consisting of heterocyclyl, amino, alkanoylamino of 1 to 6 carbon atoms in the alkyl moiety.

* * * * *